(12) United States Patent
Smyslova et al.

(10) Patent No.: US 12,290,620 B2
(45) Date of Patent: May 6, 2025

(54) DIALYSIS MACHINE CONTAINING A DEVICE FOR THE TREATMENT OF LIQUIDS, IN PARTICULAR WATER, AND METHOD FOR MONITORING THE DEVICE FOR CONTAMINATION

(71) Applicant: FRESENIUS MEDICAL CARE DEUTSCHLAND GMBH, Bad Homburg (DE)

(72) Inventors: Liubov Smyslova, Bad Homburg (DE); Gerhard Wiesen, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 963 days.

(21) Appl. No.: 17/417,388

(22) PCT Filed: Dec. 27, 2019

(86) PCT No.: PCT/EP2019/087057
§ 371 (c)(1),
(2) Date: Jun. 23, 2021

(87) PCT Pub. No.: WO2020/136230
PCT Pub. Date: Jul. 2, 2020

(65) Prior Publication Data
US 2022/0023518 A1 Jan. 27, 2022

(30) Foreign Application Priority Data
Dec. 28, 2018 (DE) .................. 10 2018 133 664.0

(51) Int. Cl.
*A61M 1/16* (2006.01)
*A61M 39/22* (2006.01)

(52) U.S. Cl.
CPC .......... *A61M 1/1672* (2014.02); *A61M 39/22* (2013.01)

(58) Field of Classification Search
None
See application file for complete search history.

(56) References Cited

U.S. PATENT DOCUMENTS 4,495,067 A * 1/1985 Klein ............... A61L 2/022
210/257.2
4,834,888 A 5/1989 Polaschegg
(Continued)

FOREIGN PATENT DOCUMENTS

| DE | 4118625 C1 | 10/1992 |
|---|---|---|
| DE | 102007004115 A1 | 8/2008 |

(Continued)

OTHER PUBLICATIONS

International Preliminary Report on Patentability issued in corresponding International Patent Application No. PCT/EP2019/087057 (English translation) dated Jul. 8, 2021 (8 pages).

(Continued)

*Primary Examiner* — Jonathan M Peo
(74) *Attorney, Agent, or Firm* — Kilyk & Bowersox, P.L.L.C.

(57) ABSTRACT

A dialysis machine is provided that includes an apparatus for treating fluids, in particular, for treating water for dialysis. The apparatus includes one or more hollow fiber membrane filters, a plurality of fluid lines, one or more sampling points, and one or more valve connections. The apparatus is configured such that contaminants can concentrate in a first hollow fiber membrane filter and conclusions can be drawn as to the contamination of the water. An analysis value can (Continued)

be determined from samples of concentrated contaminants. A method for monitoring the apparatus for contamination, is also provided.

6 Claims, 4 Drawing Sheets

(56) References Cited

U.S. PATENT DOCUMENTS

| | | | |
|---|---|---|---|
| 5,660,722 | A | 8/1997 | Nederlof |
| 6,655,394 | B1 | 12/2003 | Tanaka et al. |
| 2002/0158019 | A1 | 10/2002 | Collins et al. |
| 2002/0162778 | A1* | 11/2002 | Peabody ................. A61M 1/28 210/85 |
| 2006/0096920 | A1* | 5/2006 | Ayala ........................ C02F 1/44 210/639 |
| 2009/0217777 | A1 | 9/2009 | Hanson et al. |
| 2009/0321360 | A1 | 12/2009 | Maierhofer et al. |
| 2010/0130906 | A1* | 5/2010 | Balschat ............. A61M 1/3465 604/6.11 |
| 2010/0168640 | A1 | 7/2010 | Kopperschmidt et al. |
| 2015/0136702 | A1* | 5/2015 | Maierhofer ......... A61M 1/1609 210/96.1 |
| 2019/0125950 | A1 | 5/2019 | Noack |

FOREIGN PATENT DOCUMENTS

| | | |
|---|---|---|
| JP | 2009529392 A | 8/2009 |
| JP | 2011500101 A | 1/2011 |
| WO | 0102035 A1 | 1/2001 |
| WO | 2017182337 A1 | 10/2017 |

OTHER PUBLICATIONS

International Search Report and Written Opinion issued in corresponding International Patent Application No. PCT/EP2019/087057 (with English translation of International Search Report) dated Apr. 30, 2020 (16 pages).

Office Action issued in corresponding Japanese Patent Application No. 2021-536169 mailed Jan. 25, 2024 (with English translation)(5 pages).

https://de.wikipedia.org/w/index.php?title=Dead-End-Filtration &type, Version from Aug. 28, 20216 (with English translation)(7 pages).

* cited by examiner

DIALYSIS MACHINE CONTAINING A DEVICE FOR THE TREATMENT OF LIQUIDS, IN PARTICULAR WATER, AND METHOD FOR MONITORING THE DEVICE FOR CONTAMINATION

CROSS-REFERENCE TO RELATED APPLICATIONS

The present application is a U.S. national stage filing under 35 U.S.C. § 371, of international PCT Application No. PCT/EP2019/087057 filed Dec. 27, 2019, which in-turn claims priority to German Patent Application No. 10 2018 133 664.0 filed Dec. 28, 2018.

FIELD OF THE INVENTION

The invention relates to a dialysis machine comprising an apparatus for the treating of fluids, in particular the treating of water for dialysis, at one or more hollow fiber membrane filters as well as the correspondingly described embodiments of the apparatus itself. The invention further relates to a method for monitoring the apparatus for treating fluids, particularly water, for contamination.

BACKGROUND OF THE INVENTION

In the field of hemodialysis, large volumes of water are needed to produce dialysis fluid. Up to 120 liters of dialysis fluid is used during a normal dialysis treatment of patients with kidney disease. The dialysis fluid provided for the treatment needs to have a high degree of purity and be free of contamination in order to enable a pharmaceutically acceptable therapeutic treatment of the kidney patients. Dialysis machines are known which have a hydraulic system substantially ensuring the production, conveying and providing of dialysis fluid. In certain applications, the dialysis fluid is thereby produced within the dialysis machine from provided dialysis concentrates and treated water. The water is thereby mixed with the dialysis concentrates in a mixing chamber and converted into the ready-to-use dialysis fluid.

For hygienic reasons, water of the highest possible degree of purity is used in the producing of dialysis fluids. Ultrapure water having an electrical conductivity of $10^{-4}$ S/m or less is preferably used to produce dialysis fluid. Despite this high degree of purity. it is further necessary to treat the ultrapure water as provided by means of simple or repeated filtration and get rid of contaminants which could have harmful effects for the patient during treatment. In particular, this also refers to particulate contaminants which are not conducive to increasing the conductivity of the water. Such contaminants can for example be bacteria, viruses, endotoxins or fungi.

Thus, dialysis machines and water treatment systems for dialysis known are which comprise water treatment units in which the fluid provided at a lesser degree of purity, in particular water, is prepared for the dialysis by simple or repeated filtration as described in DE 36 41 843 A1. Additional components, e.g. dialysis concentrates, can be used to further process the thus treated fluid, in particular water, into dialysis fluids of the required degree of purity. The production of dialysis fluids can thereby start with pure water which is treated and converted with further dialysis fluid components into a ready-to-use dialysis fluid. However, it can also start from an aqueous precursor liquid which already contains components of the ready-to-use dialysis fluid, e.g. electrolytes, which is then further treated and converted with further dialysis fluid components into the ready-to-use dialysis fluid.

During the treatment of water for use in the production of dialysis fluid, a provided fluid, in particular water, is filtered through a filter. Thereby usually used are hollow fiber membrane filters having membrane properties of a nature such that contaminants present in the fluid, in particular water, can be retained by the membrane wall of the hollow fiber membrane during filtration. The hollow fiber membranes of such hollow fiber membrane filters thereby have an exclusion limit able to retain contaminants of e.g. 10 nm or 20 nm in size. Because all the contaminants are retained by filtration whenever possible, the contaminants concentrate in the hollow fiber membrane filters during the course of continuously treating the liquid, in particular water for dialysis. However, an increasing concentration of contaminants in the filters is undesirable during the water treatment. Furthermore, so-called substituate fluids are also usually prepared in dialysis from provided fluids, in particular water, by means of water purification and filtration. Such substituate fluids are administered to dialysis patients via the extracorporeal blood of the extracorporeal blood circulation. Contamination of these substituate fluids due to contaminants caused by damaged hollow fiber membrane filters of the water treatment systems then encroach directly into the organism of the patient and are thus extremely dangerous for the patient and in all cases to be prevented.

US 2009/217777 refers to the problem of detecting the potential presence of contaminants in production processes, e.g. drinking water or substances for medical use. To that end, US 2009/0217777 describes methods and an apparatus for concentrating an analyte present in a fluid. The methods comprise the steps of forming and collecting a retentate which contains an analyte. The retentate is formed by passing an analyte-containing fluid through an ultrafiltration membrane which the analyte cannot pass through due to the size exclusion. The ultrafiltration membrane separates a retentate side-area where the analyte concentrates from a permeate side-area where the filtered fluid accumulates. The retentate is collected by displacing filtrate from the permeate side of the ultrafilter membrane with gas and flushing the retentate side of the ultrafilter membrane with gas so as to produce a retentate solution containing the retentate and analytes and collecting the retentate solution.

In view of the special conditions which are to be observed in the treating of fluids or water for dialysis, the methods and apparatus known in the prior art for the monitoring and detection of contaminants in a dialysis machine prove insufficient. There is thus an ongoing need in the treatment of fluids, in particular in the treatment of water for dialysis, to make the water treatment within a dialysis machine safer for the patients from a medical standpoint. In particular, there is thus the need to be able to monitor the process of treating fluids, in particular water for dialysis, and provide a method for reliably testing the quality of the treated fluid, in particular water, as well as the contamination of the treatment system within a dialysis machine during the treatment so that the appropriate conclusions can be drawn upon inadmissibly high contamination of an apparatus for treating fluid, in particular water. If necessary, subsequent appropriate measures can then be initiated to enable preventing possible contamination of the fluid, in particular water, for example being able to replace the impacted functional parts of the treatment system.

TASK OF THE INVENTION

In a first aspect of the invention, the task is therefore providing an apparatus or respectively dialysis machine containing an apparatus for the treatment of fluids, in particular an apparatus for the treatment of water, which enables a monitoring of contaminants during the treatment of the fluid, in particular water.

In a further aspect of the invention, the task is that of providing a method for monitoring the treating of the fluids, in particular the treating of the water for the dialysis, which can determine the contamination of the apparatus or respectively dialysis machine containing an apparatus for the treatment of fluids, in particular the apparatus for the treatment of water for dialysis.

SUMMARY OF THE INVENTION

In a first aspect of the invention, the task is inventively solved with an apparatus for treating fluids, in particular water, according to an embodiment of the present invention. The present invention further relates to a dialysis machine comprising an apparatus in accordance with the present invention.

In a further aspect of the invention, the task is inventively solved by a method for monitoring the treatment of fluids, in particular water, according to another embodiment of the present invention.

In the following detailed description, the dialysis machine according to the invention and the apparatus according to the invention are always described jointly. The preferential embodiments discussed therein refer to the apparatus itself as well as the dialysis machine containing the respective apparatus.

DETAILED DESCRIPTION OF THE INVENTION

Figure 1:
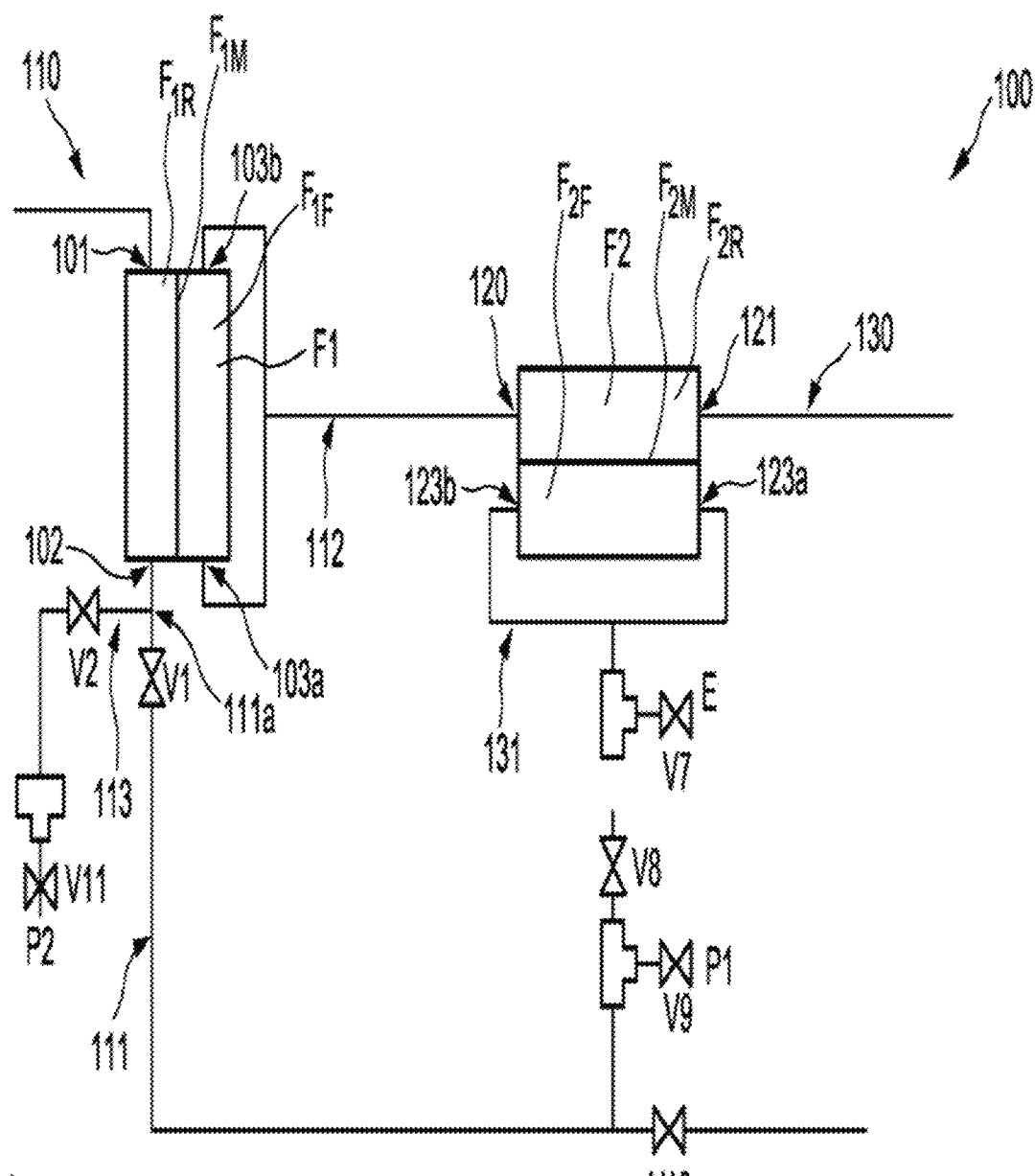
FIG. 1 is a schematic depiction of an apparatus for treating fluids, in particular, water for dialysis, in accordance with an embodiment of the present invention.

A first aspect of the invention relates to an apparatus, or respectively a dialysis machine comprising an apparatus for the treating of a fluid, in particular for the treating of water for dialysis,
which comprises a first hollow fiber membrane filter, wherein the first hollow fiber membrane filter further comprises
a plurality of hollow fiber membranes which form a retentate chamber and a filtrate chamber, wherein the retentate chamber and the filtrate chamber are separated from each other by the semipermeable membrane walls of the hollow fiber membranes,
a fluid port for the supplying of fluid, in particular water, to the retentate chamber,
a fluid port for the draining of fluid, in particular water, from the retentate chamber,
at least one fluid port for the draining of fluid, in particular water, from the filtrate chamber,
wherein the apparatus further comprises
a fluid line in fluid communication with the fluid port for supplying fluid, in particular water, to the retentate chamber of the first hollow fiber membrane filter,
a fluid line in fluid communication with the fluid port for draining fluid, in particular water, from the retentate chamber of the first hollow fiber membrane filter,
a fluid line in fluid communication with the fluid port for draining fluid, in particular water, from the filtrate chamber of the first hollow fiber membrane filter,
a first valve connection in engagement with the fluid line for draining fluid, in particular water, from the retentate chamber, wherein the valve connection has at least two valve positions, by means of which the flow of fluid through the fluid line for draining fluid from the retentate chamber can be blocked or conducted,
optionally further comprising
a first fluid branching point in the fluid line for draining fluid, in particular water, from the retentate chamber of the first hollow fiber membrane filter in fluid communication with a first branching fluid line, a second valve connection in engagement with the first branching fluid line, wherein the second valve connection has at least two valve positions, by means of which the flow of fluid, in particular water, through the first branching fluid line can be blocked or conducted, characterized in that
a sampling point is arranged downstream the first valve connection in fluid communication with the fluid line for draining fluid, in particular water, from the retentate chamber,
and/or that
a second sampling point is arranged downstream the second valve connection in fluid communication with the first branching fluid line.

The apparatus defined herein can be utilized as part of a water treatment unit in a dialysis machine.

The apparatus or respectively dialysis machine comprising an apparatus according to the first aspect of the invention has the advantage of allowing samples to be drawn during a dialysis machine treatment method on a fluid, in particular water for dialysis, by a regulating of the first valve connection to be able to take samples and supply same for the contamination analysis. In particular, by setting the first valve connection into a blocking position, the fluid, in particular water, is introduced in the retentate chamber of the first hollow fiber membrane filter and undergoes "dead-end" filtration. The introduced fluid, in particular water, passes through the membrane wall into the filtrate chamber and is thereby filtered. The hollow fiber membranes of the first hollow fiber membrane filter are thereby designed such that contaminants are retained by the membrane wall of the hollow fiber membranes during the "dead-end" filtration and concentrate in the retentate chamber.

The introducing of the fluid, in particular water, into the retentate chamber of the first hollow fiber membrane filter and the passing of the fluid, in particular water, through the membrane wall of the hollow fiber membranes into the filtrate chamber can be realized with suitable pumping means such as, for example, tube roller pumps, gear pumps or impeller pumps. One skilled in the art is familiar with suitable and common pumping means in the field of dialysis technology.

The concentration of contaminants in the retentate chamber of the first hollow fiber membrane filter can be checked by setting the valve position of the first valve connection such that fluid can be drained off through the fluid line for draining fluid from the retentate chamber. In this valve connection setting, the concentrated contaminants are flushed from the retentate chamber and can be sampled downstream of the first valve connection via a first sampling point and the sample submitted to an analysis. In the process, any given valve position of the second valve connection remains in a blocking position.

Alternatively, the concentration of the contaminants in the retentate chamber of the first hollow fiber membrane filter can be also checked by the valve position of the first valve connection remaining in a blocking position and the valve position of the second valve connection being brought into a conducting valve position. With this valve connection setting, the concentrated contaminants are flushed from the retentate chamber and can be sampled via the second sampling point and the sample submitted to an analysis.

Advantageously, a sample may be repeatedly drawn from the first or second sampling point from predetermined amounts of fluid, in particular water, conveyed to the filtrate chamber via the membrane walls of the hollow fiber membranes and examined for possible contamination and conclusions drawn as to the degree of contamination of the system or the fluid provided, in particular water. As long as a low contamination is to be expected in the provided fluid, contaminants can continue to concentrate in the retentate chamber for a long period of time until the contaminant concentration rises above an analytically possible detection limit and a contamination can thus be reliably confirmed which would be undetected in the absence of such a concentration. This is important in dialysis treatment from a hygienic perspective since harmful effects for the patient due to contamination can already begin to set in below a detectable amount of contaminants. The concentration of contaminants thus allows the conclusion of whether or not the available fluid, in particular water, already exhibits an inadmissibly high degree of contamination. In practice, the predetermined volume obtained as filtrate via the filtrate chamber of the first hollow fiber membrane filter as described above can amount to, depending on the degree of contamination to the available fluid, in particular water, 20 or more liters, 30 or more liters, 50 or more liters, 100 or more liters, or 200 or more liters.

A hollow fiber membrane filter with hollow fiber membranes is used in the apparatus for the treating of a fluid, the membrane property of which is characterized by contaminant retention capability. The pore size of the hollow fiber membrane's selective layer thereby relates to contaminant retentivity. To be understood as a "hollow fiber membrane" in this context is a hollow fiber having a porous wall and permeability to fluids, particularly water. Should viruses, for example, also be retained during the fluid treatment, the use of hollow fiber membranes having a maximum average pore size smaller than 20 nm, preferably smaller than 10 nm, is advisable.

Usable hollow fiber membrane filters according to the invention and the structural details of such hollow fiber membrane filters are sufficiently well known to the skilled person from the prior art. Reference is made to DE3641843A1 in conjunction hereto.

In the hollow fiber membrane filter used according to the invention, the interior of the filter module is divided into a "retentate chamber" and a "filtrate chamber" which are separated from each other by the membrane wall of the hollow fiber membranes and by the hard encapsulated areas at the end. The "retentate chamber" of the filter module is provided for the retention of the contaminants. The fluid to be treated can reach the "filtrate chamber" by filtration through the membrane wall. Non-filtered fluid and contaminants remain in the retentate chamber and are referred to as "retentate." The fluid reaching the filtrate chamber by crossing the membrane wall is referred to as "filtrate."

To be understood by "dead-end" filtration in the sense of the invention is a method in which fluid, in particular water, is introduced into the retentate chamber of the hollow fiber membrane filter via a fluid port while at the same time, however, the draining of fluid from the retentate chamber is blocked by the blocking position of the first valve. The fluid, in particular water, flowing into the retentate chamber, is then conducted through the membrane wall into the filtrate chamber by a building pressure gradient. With hollow fiber membrane filters, the "dead-end" method is usually realized by introducing fluid via a fluid inlet into the hollow fiber membrane filter on the lumen side of the hollow fiber membranes. The ends of the hollow fiber membranes are thereby sealed or blocked so that no liquid can leak out of the ends of the hollow fiber membranes. In particular, the second fluid inlet at the other end of the hollow fiber membrane filter is often blocked so that all the fluid to be filtered can pass the membrane wall and be drained off as filtrate.

As defined by the present application, a "fluid port" refers to a connection to the filter module via which the fluid, in particular the water for the dialysis, can be introduced into the hollow fiber membrane filter, e.g. either into the retentate chamber or the filtrate chamber. A fluid inlet termed as such is also equally suited to draining fluid, in particular draining filtrate or retentate from the retentate chamber or filtrate chamber of a filter module.

Pumping means pumps the provided fluid, in particular the provided water, into the retentate chamber. As defined by the present application, "pumping means" refers to any means able to pump liquids by pressure change. The inventive method in particular provides for the use of membrane pumps or peristaltic pumps, in particular tube roller pumps, as is sufficiently familiar in the field of medical technology. To be understood in general in the sense of the present application is that suitable pumping means support the supplying and draining of fluids through the fluid lines, valve connections, fluid ports and hollow fiber membrane filter when doing so is necessary for treating the fluid, in particular water.

Any connecting system suitable for conveying the fluid, in particular water, provided in the inventive apparatus can serve as the "fluid lines." Flexible hose or tubing systems as known in medical technology, particularly in dialysis, can in particular serve as fluid lines.

As defined by the present application, "fluid branching point" refers to the convergence of at least three fluid lines into one structural unit. Corresponding structural elements in dialysis technology such as e.g. so-called "T-pieces" or "Y-pieces" are familiar to the skilled person. Accordingly, a fluid branching point is to be understood as fluid conducted through a fluid line being conducted further in at least two further fluid lines. Also to be understood as a fluid branching point in the sense of the present application is fluid which is conducted through at least two fluid lines being conducted further in one further fluid line.

As defined by the present application, the terms "upstream" and "downstream" refer to a direction of travel of the fluid, in particular water, conducted through the inventive apparatus. In the understanding of the present application, the "direction of travel" is aligned to the base flow direction of the fluid, in particular water, in the inventive apparatus in terms of a treatment and any potential repeated filtration of the provided fluid, in particular water. Understood here as "base flow direction" is:

- the conducting of fluid, in particular water, through a fluid line and fluid port into the retentate chamber of a hollow fiber membrane filter,
- the draining of the fluid, in particular water, from the retentate chamber of the hollow fiber membrane filter if applicable,
- the passing of fluid, in particular water, through the membrane wall into the filtrate chamber of the hollow fiber membrane filter,
- the draining of fluid, in particular water, from the filtrate chamber of a hollow fiber membrane filter through a fluid port and fluid line,
- the conducting of fluid, in particular water, to extraction and sampling points through branching fluid lines if applicable.

A direction of travel along this described direction of flow is referred to as "upstream."A direction of travel opposite to this described direction of flow is referred to as "downstream." Flow directions running opposite to the above-described direction of flow are also described in the present application. According to the present application, the terms "upstream" and "downstream" are not applicable to these opposite flow directions.

As defined by the present application, the term "treatment of a fluid," in particular "treatment of water," is to be understood as a method in which impurities, in particular contaminants, in a provided fluid, particularly water, are depleted in order to make the treated fluid, or in particular the treated water, available for further use. "Depletion" refers to a decreasing of the concentration of impurities or contaminants. Using the example of treating water for dialysis, this might mean subjecting drinking water, e.g. provided through a city or district public water supply system, to further purification in order to make it available for use in the therapeutic treatment of dialysis patients. The required water quality for dialysis is outlined in the ISO13359:2014 standard, the required quality for dialysis fluid is outlined in the ISO11663:2014 standard. In particular, water also can be provided by an ion exchanger or a reverse osmosis system.

In one embodiment according to the first aspect of the invention, the inventive apparatus, or respectively dialysis machine comprising an apparatus, is characterized by a second fluid branching point being arranged from the fluid line for supplying fluid, in particular water, to the retentate chamber upstream of the first hollow fiber membrane filter, further characterized by a third fluid branching point being arranged in the fluid line for draining fluid, in particular water, from the filtrate chamber of the first hollow fiber membrane filter, further characterized by the second fluid branching point on the fluid line for supplying fluid, in particular water, into the retentate chamber ($F_{1R}$) of the first hollow fiber membrane filter and the third fluid branching point on the fluid line for the draining of fluid, in particular water, from the filtrate chamber of the first hollow fiber membrane filter being fluidly connected by a fluid line, further characterized by a third valve connection being arranged in engagement with the fluid line between the second fluid branching point and the third fluid branching point, wherein the third valve connection has at least two valve positions, by means of which the flow of fluid, in particular water, through the fluid line between the second fluid branching point and the third fluid branching point can be blocked or conducted, further characterized by a fourth valve connection being arranged downstream the third fluid branching point in engagement with the fluid line for draining fluid, in particular water, from the filtrate chamber, wherein the fourth valve connection has at least two valve positions, by means of which the flow of fluid, in particular water, through the fluid line for draining fluid, in particular water, from the filtrate chamber can be blocked or conducted.

According to this embodiment, it is possible to make the contaminants of the at least first hollow fiber membrane filter as concentrated in the retentate chamber available in a simultaneous preflushing and backflushing process and sample extraction. In terms of the present embodiment, a "preflushing process" is to be understood as the retentate chamber of a hollow fiber membrane filter being flushed with fluid, in particular water, through the fluid ports for supplying and draining fluid, in particular water, in and out of the retentate chamber. The contaminants can thus be drained from the retentate chamber and retrieved via sampling at the first sampling point and supplied to the analysis.

In terms of the present embodiment, a "backflushing process" is to be understood as fluid, in particular water, being conducted into the filtrate chamber of a hollow fiber membrane filter and from there conducted into the retentate chamber via the membrane walls of the hollow fiber membranes. From there, the fluid, in particular water, can be drained via the fluid port and the fluid line for draining fluid from the retentate chamber and conducted to the previously described first or second sampling point at which samples can be retrieved and analyzed for contamination.

Advantageously, contaminants in the retentate chamber of the first hollow fiber membrane filter which adhere in the membrane wall of the hollow fiber membranes and which the preflushing process alone has difficulty in flushing can also be flushed out via the backflushing process. The simultaneous preflushing and backflushing thus enables a higher accuracy to the detecting of contaminants in the retentate chamber of the first hollow fiber membrane filter by sampling and analysis.

In a further embodiment according to the first aspect of the invention, the inventive apparatus or respectively dialysis machine is characterized in that a fifth valve connection is arranged in the apparatus for treating fluids, in particular water for the dialysis, upstream of the first hollow fiber membrane filter between the second fluid branching point of the fluid line for supplying fluid, particularly water, to the retentate chamber of the first hollow fiber membrane filter and the first hollow fiber membrane filter itself in engagement with the fluid line for supplying fluid, in particular water, to the retentate chamber of the first hollow fiber membrane filter, whereby the fifth valve connection has at least two valve positions, by means of which the flow of fluid, in particular water, through the fluid line for supplying fluid, in particular water, to the retentate chamber of the first hollow fiber membrane filter can be blocked or conducted.

According to this embodiment, the first hollow fiber membrane filter can undergo alternating preflush and backflush processes; additionally, the preflushing and backflushing can also be performed simultaneously. To conduct the preflushing process, the valve positions of the first and fifth valve connection are set to a conducting position and the valve positions of the third and fourth valve connection to a blocking position. Fluid, in particular water, is conducted through the retentate chamber and contaminants can be accordingly analyzed for contamination via sampling at the first sampling point or second sampling point.

To perform the backflushing process, the third and fifth valve connection are set to a conducting valve position and fluid, in particular water, is conducted into the filtrate chamber of the hollow fiber membrane filter, carried into the retentate chamber via the membrane wall. The samples can be taken at the first sampling point or the third sampling point. For improved flushing of the contaminants from the retentate chamber of the first hollow fiber membrane filter, the preflushing and backflushing can alternate and repeat.

To perform the preflushing and backflushing process simultaneously, the fifth, third, fourth and first valve position are set to a conducting valve position.

In a further embodiment according to the first aspect of the invention, the inventive apparatus or respectively dialysis machine comprising the apparatus for treating fluids, in particular water for the dialysis, is characterized by the apparatus further comprising the following
at least one second hollow fiber membrane filter,
comprising a plurality of hollow fiber membranes with a retentate chamber and a filtrate chamber separated from each other by semipermeable membrane walls of the hollow fiber membranes,
wherein the second hollow fiber membrane filter comprises a fluid port for the supply of fluid, in particular water, into the retentate chamber of the second hollow fiber membrane filter,
a fluid port for the draining of fluid, in particular water, from the retentate chamber of the second hollow fiber membrane filter,
at least one fluid port for the draining of fluid, in particular water, from the filtrate chamber of the second hollow fiber membrane filter,
and wherein the apparatus further comprises
a fluid line in fluid communication with the fluid port for supplying fluid, in particular water, into the retentate chamber of the second hollow fiber membrane filter,
a fluid line in fluid communication with the fluid port for draining fluid, in particular water, from the retentate chamber of the second hollow fiber membrane filter,
a fluid line in fluid communication with the at least one fluid port for draining fluid, in particular water, from the filtrate chamber of the second hollow fiber membrane filter,
wherein the apparatus is further characterized by the fluid line in fluid communication with the fluid port for supplying fluid, in particular water, into the retentate chamber of the second hollow fiber membrane filter being fluidly connected to the fluid line for draining fluid, in particular water, from the filtrate chamber of the first hollow fiber membrane filter.

By setting the first valve connection and the third valve connection into a blocking valve position and setting the fifth valve connection and fourth valve connection into a conducting valve position, fluid, in particular water, is introduced into the retentate chamber of the second hollow fiber membrane filter via the retentate chamber and the filtrate chamber of the first hollow fiber membrane filter. By the fluid, particularly water, passing the membrane walls of the hollow fiber membranes of the second hollow fiber membrane filter from the retentate chamber into the filtrate chamber of the second hollow fiber membrane filter, said fluid, in particular water, undergoes a second filtration. The second filtration thereby preferably ensues as a "tangential flow" process. In addition, purified water can be taken from the second filter in order to use it as a substituate fluid in a dialysis mode known as hemodiafiltration. That means that the substituate is infused into the patient's body. There are therefore particularly high requirements as to the substituate's purity and sterility which necessitate a particularly sensitive measuring method for determining contaminants.

According to the present application, the "tangential flow" filtration or method means that the fluid to be filtered is conducted along the membrane surface of the hollow fiber membranes within the hollow fiber membrane filter. A portion of the fluid thereby passes through the membrane wall as filtrate on the filtrate side. A further portion of the fluid remains on this side of the membrane wall in the retentate chamber and is drained from the filter as so-called retentate. Hence, fluid is introduced into the retentate chamber of the second hollow fiber membrane filter in this arrangement and a portion of the fluid is drained off via the fluid port for draining fluid from the retentate chamber. A further portion passes through the membrane wall of the hollow fiber membranes into the filtrate chamber of the second hollow fiber membrane filter and is drained off via the fluid port and fluid line for draining fluid from the filtrate chamber of the second hollow fiber membrane filter.

Advantageously, treated fluid, which has undergone two treatment filtration stages, can be sampled at an extraction point in fluid communication with the fluid line for draining fluid, in particular water, from the filtrate chamber of the second hollow fiber membrane filter and made available for the production of substituate fluid.

In a further embodiment according to the first aspect of the invention, the inventive apparatus or respectively dialysis machine comprising the apparatus for treating a fluid, in particular water, is characterized by a fourth fluid branching point, from which branches a second branching fluid line, being arranged in the fluid line between the fluid port for draining fluid, in particular water, from the retentate chamber of the second hollow fiber membrane filter, further characterized by a sixth valve connection in engagement with the fluid line for draining fluid, in particular water, from the retentate chamber of the second hollow fiber membrane filter being arranged downstream of the fourth fluid branching point,
wherein the sixth valve connection has at least two valve positions, by means of which the flow of fluid, particularly water, through the fluid line for draining fluid, particularly water, from the retentate chamber of the second hollow fiber membrane filter can be blocked or conducted,
further characterized by the second branching fluid line being in fluid communication with a fourth sampling point.

By setting the sixth valve connection to a blocking position, the fluid, in particular water, drained from the retentate chamber of the second hollow fiber membrane filter is conducted to the fourth sampling point via the second branching line. Samples can be retrieved at the fourth sampling point and supplied for analysis. In accordance with the apparatus of this embodiment, the retentate chamber of the second hollow fiber membrane filter can be analyzed for contamination. In particular, it can also be checked whether the fluid from the first filtration stage passed from the retentate chamber and filtrate chamber of the first hollow fiber membrane filter to the retentate chamber of the second hollow fiber membrane filter via "dead-end" filtration is contaminated. Determining the contaminants in the samples taken at the sampling point thus allows drawing conclusions as to the filtration quality of the first hollow fiber membrane filter.

In a further embodiment in accordance with the preceding implementation according to the first aspect of the invention, the inventive apparatus or respectively dialysis machine comprising the apparatus for treating a fluid, in particular water for the dialysis, is characterized by a second fluid branching point being arranged from the fluid line for supplying fluid, in particular water, to the retentate chamber of the first hollow fiber membrane filter upstream of the first hollow fiber membrane filter (F1), further characterized by the apparatus comprising a fifth fluid branching point on the fluid line for draining fluid, in particular water, from the filtrate chamber of the second hollow fiber membrane filter, further characterized by a fluid line being arranged in fluid communication with the second fluid branching point on the fluid line for supplying fluid, in particular water, to the retentate chamber of the first hollow fiber membrane filter and the fifth fluid branching point on the fluid line for draining fluid, in particular water, from the filtrate chamber of the second hollow fiber membrane filter, further characterized by a third valve connection being arranged in engagement with the fluid line between the second fluid branching point on the fluid line for supplying fluid, in particular water, to the retentate chamber of the first hollow fiber membrane filter and the fifth fluid branching point on the fluid line for draining fluid, in particular water, from the filtrate chamber of the second hollow fiber membrane filter, wherein the third valve connection has at least two valve positions, by means of which the flow of fluid, particularly water, through the fluid line between the second fluid branching point and the fifth fluid branching point can be blocked or conducted, further characterized by the fluid port for supplying fluid, in particular water, to the retentate chamber of the second hollow fiber membrane filter is in fluid communication with the fluid port for draining fluid, in particular water, from the filtrate chamber of the first hollow fiber membrane filter via a fluid line, further characterized by a fifth valve connection being arranged upstream the filter between the second fluid branching point in engagement with the fluid line for the supply of fluid, in particular water, into the retentate chamber and the first hollow fiber membrane filter, wherein the fifth valve connection has at least two valve positions, by means of which the flow of fluid, particularly water, in the fluid line for supplying fluid, particularly water, to the retentate chamber can be blocked or conducted.

One advantage of this embodiment is that the retentate chamber of the second hollow fiber membrane filter can be checked for contamination after preflushing by sampling and analysis. In the process, the third valve connection and the first valve connection are set to a blocking valve position and the fifth valve connection set to a conducting valve position. To check for contamination, fluid, particularly water, is introduced into the retentate chamber of the first hollow fiber membrane filter, passed over the membrane wall of the hollow fiber membranes of the first hollow fiber membrane filter in the "dead-end" process, and introduced into the retentate chamber of the second hollow fiber membrane filter. Samples can be taken from the fluid subsequently drained from the retentate chamber of the second hollow fiber membrane filter and checked for contamination.

In a further alternative, the fifth valve connection can be set into a blocking valve position and the third valve connection can be set to a conducting valve position. According to this arrangement of the valve connection, fluid, in particular water, is introduced into the filtrate chamber of the second hollow fiber membrane filter and passed over the membrane wall into the retentate chamber of the second hollow fiber membrane filter pursuant to a backflushing process. Contaminants adhering to the membrane wall of the hollow fiber membranes of the second hollow fiber membrane filter can thus be flushed out and analyzed for contamination by sampling, e.g. at the fourth sampling point.

In one of the embodiments described herein, the apparatus, or dialysis machine respectively, comprises an analysis apparatus, with which an analysis value relative to the concentration of contaminants in a respective sample can be obtained from a sample obtained at the sampling points. In particular, such an analysis apparatus is arranged at the sampling point downstream of the first valve connection in fluid communication with the fluid line for draining fluid, particularly water, from the retentate chamber of the first hollow fiber membrane filter. Additionally, the apparatus, respectively dialysis machine comprising the apparatus as described in an embodiment, can be configured so as to comprise the means for determining the volume of fluid, in particular water, passed from the retentate chamber to the filtrate chamber of the first hollow fiber membrane filter. Additionally, the apparatus or dialysis machine comprising the apparatus as described in an embodiment respectively can be configured so as to comprise means for determining the volume of fluid, in particular water, with which the contaminants are flushed to the sampling point. Additionally, the apparatus, respectively dialysis machine, can comprise an electronic evaluation unit.

The evaluation unit is configured so as to determine a conversion factor from the analysis value on the concentration of contaminants in a respective sample, the volume of fluid, in particular water, passed from the retentate chamber into the filtrate chamber of the first hollow fiber membrane filter, and the volume of fluid, in particular water, with which the contaminants are flushed to the sampling point. The evaluation unit is thus suitable for determining the volume of fluid, in particular water for dialysis, to be conducted from the retentate chamber to the filtrate chamber of the first hollow fiber membrane filter prior to the initiating of a flushing process for the analysis. The conversion factor thus provides a value for the concentration of contaminants. If an analysis value on the concentration of contaminants in a respective sample is for example indicated in CFU/ml (colony-forming units per milliliter), then the conversion factor can be used to determine a contamination value for the fluid, in particular water, supplied to the apparatus or dialysis machine respectively. It is also possible to determine non-integer values. In particular, extremely low values unable to be determined by direct analysis of the provided fluid, particularly water, can also be reliably determined.

In a second aspect, the invention relates to a method for monitoring the treatment of fluids, in particular the treatment of water for dialysis, in an apparatus or dialysis machine respectively which comprises the steps providing an apparatus according to the first aspect of the invention, setting the first valve connection and the potential second valve connection into a blocking position, introducing fluid, particularly water, into the retentate chamber of the hollow fiber membrane filter, filtering the fluid, in particular water, across the membrane wall of the hollow fiber membranes from the retentate chamber to the filtrate chamber of the first hollow fiber membrane filter and collecting fluid, in particular water, in the filtrate chamber, whereby contaminants in the untreated water are retained by the hollow fiber membrane during filtration, draining the fluid, in particular water, from the filtrate chamber, setting the first valve connection to a conducting position after a predetermined volume of fluid, in particular water, has passed into the filtrate chamber by filtration,
wherein the second valve connection, if applicable, remains in a blocking valve position,
introducing further fluid, particularly water, into the retentate chamber of the first hollow fiber membrane filter,
characterized by samples being taken at the first sampling point downstream of the first valve connection and the samples analyzed for contamination,
or, where applicable,
setting the first valve connection to a blocking valve position and setting the second valve connection to a conducting valve connection after a predetermined volume of fluid, in particular water, has passed into the filtrate chamber of the first hollow fiber membrane filter by filtration,
introducing further fluid, particularly water, into the retentate chamber of the first hollow fiber membrane filter,
characterized by samples being taken at the second sampling point downstream of the first fluid branching point and the samples analyzed for contamination.

According to the inventive method, a large volume of fluid, in particular water, can be filtered and a concentration of contaminants corresponding to the volume of filtered fluid, in particular water, thereby obtained. The starting contamination of the fluid, in particular water, can as a result be concluded according to the described method.

Within the meaning of the present application, the terms "filtration" or "filtering" refer to the passing of fluid from the retentate chamber to the filtrate chamber past the membrane wall of the hollow fiber membranes of the hollow fiber membrane filter, whereby components, in particular contaminants, which are present in the fluid, in particular water, are retained by the membrane wall.

In further embodiment of the second aspect, the invention thus relates to a method for monitoring the treatment of fluid, in particular water for dialysis, wherein the predetermined volume of fluid, in particular water, passed by filtration into the filtrate chamber of the first hollow fiber membrane filter amounts to at least 20 l or more, preferentially at least 100 l or more, further preferentially at least 200 l or more.

In further embodiment according to the second aspect, the invention relates to a method for monitoring the treatment of fluid, in particular water for dialysis, comprising the steps
providing an apparatus according to an embodiment of the first aspect of the invention,
setting the first valve connection to a blocking valve position,
setting the third valve connection to a blocking valve position,
setting the fourth valve connection to a conducting valve position,
introducing fluid, in particular water, into the retentate chamber of the first hollow fiber membrane filter,
filtering the fluid, in particular water, across the membrane wall of the hollow fiber membranes of the first hollow fiber membrane filter, whereby contaminants in the fluid, in particular water, are retained by the membrane wall of the hollow fiber membranes during the filtration,
passing fluid, in particular water, from the filtrate chamber of the first hollow fiber membrane filter to the retentate chamber of the second hollow fiber membrane filter,
filtering the fluid, in particular water, in the retentate chamber of the second hollow fiber membrane filter through the membrane wall of the hollow fiber membranes of the second hollow fiber membrane filter, whereby contaminants in the fluid are retained by the membrane wall of the hollow fiber membranes of the second hollow fiber membrane filter during the filtration,
draining fluid, in particular water, out of the filtrate chamber of the second hollow fiber membrane filter,
if needed, drawing fluid, in particular water, or samples at an extraction point connected to the fluid line for draining fluid, in particular water, from the filtrate chamber of the second hollow fiber membrane filter,
subsequently setting the first valve connection to a conducting valve position,
setting the third valve connection to a conducting valve position,
setting the fourth valve connection to a blocking valve position,
setting the first valve connection to a conducting valve position,
after a predetermined volume of fluid, in particular water, has passed to the filtrate chamber by filtration,
filtering the fluid, in particular water, in the filtrate chamber of the first hollow fiber membrane filter through the membrane wall of the hollow fiber membranes of the first hollow fiber membrane filter into the retentate chamber of the first hollow fiber membrane filter, whereby contaminants are flushed from the retentate chamber of the first hollow fiber membrane filter during the filtration,
draining fluid out of the retentate chamber of the first hollow fiber membrane filter,
characterized by samples being taken at the first sampling point downstream of the first valve connection and the samples analyzed as to contamination.

The method has the advantage of simultaneously flushing the retentate chamber and the filtrate chamber of the first hollow fiber membrane filter in the simultaneous preflushing and backflushing process subsequent the concentrating of contaminants in the first hollow fiber membrane filter as described above.

In a further embodiment according to the second aspect, the invention relates to a method for monitoring the treatment of fluid, in particular water for dialysis, comprising the steps
providing an apparatus according to an embodiment of the first aspect of the invention,
setting the first valve connection to a blocking valve position,
setting the fifth valve connection to a conducting valve position,
setting the third valve connection to a blocking valve position,
setting the fourth valve connection to a conducting valve position,
introducing fluid, in particular water, into the retentate chamber of the first hollow fiber membrane filter,
filtering the fluid, in particular water, through the membrane wall of the hollow fiber membranes of the first hollow fiber membrane filter, whereby contaminants in the fluid, in particular water, are retained by the membrane wall of the hollow fiber membranes during the filtration,
passing fluid, in particular water, from the filtrate chamber of the first hollow fiber membrane filter to the retentate chamber of the second hollow fiber membrane filter,
filtering the fluid, in particular water, in the retentate chamber of the second hollow fiber membrane filter through the membrane wall of the hollow fiber membranes of the second hollow fiber membrane filter, whereby contaminants in the fluid are retained by the membrane wall of the hollow fiber membranes of the second hollow fiber membrane filter during the filtration, draining fluid, in particular water, out of the filtrate chamber of the second hollow fiber membrane filter, if needed, drawing fluid, in particular water, or samples at the extraction point connected to the fluid line for draining fluid, in particular water, from the filtrate chamber of the second hollow fiber membrane filter and, if applicable, analyzing the sample as to contamination, subsequently setting the first valve connection to a conducting valve position, setting the fifth valve connection to a blocking valve position, setting the third valve connection to a conducting valve position, setting the fourth valve connection to a blocking valve position, after a predetermined volume of fluid, in particular water, has passed to the filtrate chamber by filtration, filtering the fluid, in particular water, in the filtrate chamber of the first hollow fiber membrane filter through the membrane wall of the hollow fiber membranes of the first hollow fiber membrane filter into the retentate chamber of the first hollow fiber membrane filter, whereby contaminants are flushed from the retentate chamber of the first hollow fiber membrane filter during the filtration, draining fluid out of the retentate chamber of the first hollow fiber membrane filter, characterized by samples being taken at the first sampling point downstream of the first valve connection and the samples analyzed as to contamination.

The preflushing and backflushing of the first hollow fiber membrane filter according to the described method of this embodiment can be carried out alternatingly or simultaneously and repetitively subsequent contaminant accumulation. The method has the advantage of an improved flushing of the hollow fiber membrane filter of contamination, which is in particular advantageous at low levels of contamination.

In a further embodiment according to the second aspect, the invention relates to a method for monitoring the treatment of fluid, in particular water for dialysis, comprising the steps providing an apparatus according to an embodiment of the first aspect of the invention, setting the first valve connection to a blocking valve position, setting the sixth valve connection to a conducting valve position, introducing fluid, in particular water, into the retentate chamber of the first hollow fiber membrane filter, filtering fluid, in particular water, through the membrane wall of the hollow fiber membranes from the retentate chamber to the filtrate chamber of the first hollow fiber membrane filter and collecting fluid in the filtrate chamber, whereby contaminants in the fluid, in particular water, are retained by the hollow fiber membrane during the filtration, passing fluid, in particular water, from the filtrate chamber of the first hollow fiber membrane filter to the retentate chamber of the second hollow fiber membrane filter, setting the sixth valve connection to a blocking valve position after a predetermined volume of fluid, in particular water, has passed to the filtrate chamber of the first hollow fiber membrane filter by filtration, further introducing of fluid, in particular water, into the retentate chamber of the first hollow fiber membrane filter, filtering of fluid, in particular water, in the filtrate chamber of the first hollow fiber membrane filter, passing of fluid, in particular water, from the filtrate chamber of the first hollow fiber membrane filter to the retentate chamber of the second hollow fiber membrane filter, characterized by samples being taken at the fourth sampling point (P4) and the samples analyzed as to contamination.

The method has the advantage of the retentate chamber of the second hollow fiber membrane filter being able to be checked for contamination subsequent the accumulating of contaminants in the first hollow fiber membrane filter and/or second hollow fiber membrane filter as described above.

In a further embodiment according to the second aspect, the invention relates to a method for monitoring the treatment of fluid, in particular water for dialysis, comprising the steps providing an apparatus of an embodiment according to the first aspect of the invention, setting the first valve connection to a blocking valve position, setting the fifth valve connection to a conducting valve position, setting the third valve connection to a blocking valve position, setting the sixth valve connection to a conducting valve position, introducing fluid, in particular water, into the retentate chamber of the hollow fiber membrane filter, filtering the fluid, in particular water, through the membrane wall of the hollow fiber membranes from the retentate chamber to the filtrate chamber of the first hollow fiber membrane filter and collecting fluid, in particular water, in the filtrate chamber, whereby contaminants in the fluid, in particular water, are retained by the hollow fiber membrane during the filtration, passing fluid, in particular water, from the filtrate chamber of the first hollow fiber membrane filter to the retentate chamber of the second hollow fiber membrane filter, filtering fluid, in particular water, through the membrane wall of the hollow fiber membranes from the retentate chamber to the filtrate chamber of the second hollow fiber membrane filter and collecting fluid, in particular water, in the filtrate chamber of the second hollow fiber membrane filter, whereby contaminants in the untreated water are retained by the hollow fiber membrane during the filtration, draining water out of the filtrate chamber of the second hollow fiber membrane filter and, if needed, drawing fluid, in particular water, or samples at the extraction point connected to the fluid line for draining fluid, in particular water, from the filtrate chamber of the second hollow fiber membrane filter and, if applicable, analyzing the sample as to contamination, subsequently setting the fifth valve connection to a blocking valve position, setting the third valve connection to a conducting valve position, setting the sixth valve connection to a blocking valve position, after a predetermined volume of fluid, in particular water, has passed to the filtrate chamber by filtration, introducing fluid, in particular water, into the filtrate chamber of the second hollow fiber membrane filter, filtering fluid, in particular water, through the membrane wall of the hollow fiber membranes from the filtrate chamber to the retentate chamber of the second hollow fiber membrane filter and collecting fluid, in particular water, in the retentate chamber of the second hollow fiber membrane filter, whereby contaminants retained by the hollow fiber membrane are flushed out of the retentate chamber of the second hollow fiber membrane filter during the filtration, characterized by samples being taken at the fourth sampling point and the samples analyzed as to contamination.

The method has the advantage of checking the retentate chamber of the second hollow fiber membrane filter for contamination after the accumulating of contaminants in the first hollow fiber membrane filter and/or second hollow fiber membrane filter as described above by backflushing the second hollow fiber membrane filter. Contaminants can be flushed out after accumulation and analyzed with greater accuracy by way of the backflushing process, which is advantageous at lower contaminations.

In a further embodiment according to the second aspect, the invention relates to a method for monitoring the treatment of fluid, in particular water for dialysis, comprising a step in which a conversion factor is determined with which an analysis value can be indicated for the fluid, in particular water, provided to the apparatus or respectively dialysis machine. Specifically, it is provided for a sample to be taken at one of the sampling points and an analysis value relative to the concentration of contaminants be determined by means of an analysis apparatus, whereby further determined is the volume of fluid, in particular water, passed from the retentate chamber to the filtrate chamber of the first hollow fiber membrane filter, whereby further determined is the volume of fluid, in particular water, with which the contaminants are flushed to the sampling point, characterized in that a conversion factor is determined by means of an electronic evaluation unit configured to determine the volume of fluid, in particular water, passed from the retentate chamber to the filtrate chamber of the first hollow fiber membrane filter and the volume of fluid, in particular water, with which the contaminants are flushed to the sampling point from the analysis value on the contaminant concentration in a respective sample and, if applicable, a contamination value for the fluid, in particular water, supplied to the apparatus or dialysis machine respectively.

It is thus possible to determine the volume of the water for dialysis which passes through the filter before a flushing process for the analysis commences. The conversion factor thus provides a value for the degree of contaminant concentration. If an analysis value on the concentration of contaminants in a respective sample is for example indicated in CFU/ml (colony-forming units per milliliter), then the conversion factor can be used to determine a contamination value for the fluid, in particular water, supplied to the apparatus or dialysis machine respectively. It is also possible to determine non-integer values. In particular, extremely low values unable to be determined by direct analysis of the provided fluid, particularly water, can also be reliably determined.

DESCRIPTION OF THE INVENTION REFERENCING THE FIGURES

Further details and embodiments of the invention will be described in the following with reference to the figures. For purposes of illustrating the invention, the dialysis machine according to the invention is not shown within the figures. The apparatus as are depicted in the figures are typically arranged within the dialysis machine.

FIG. 1 shows a schematic depiction of one inventive embodiment of an apparatus according to the present invention. In FIG. 1, the 100 indicates the apparatus for treating fluids, in particular water for dialysis. F1 indicates a hollow fiber membrane filter having a plurality of hollow fiber membranes. Shown schematically are the retentate chamber $F_{1R}$ and the filtrate chamber $F_{1F}$ of the hollow fiber membrane filter F1 formed by the membrane wall $F_{1M}$ of the plurality of hollow fiber membranes (not shown in the illustration). FIG. 1 further shows the fluid port 101 and the fluid line 110 for supplying fluid, in particular water, to the retentate chamber $F_{1R}$ of the first hollow fiber membrane filter F1. FIG. 1 further shows fluid port 102 and fluid line 111 for draining fluid, in particular water, from the retentate chamber $F_{1R}$ of the hollow fiber membrane filter, at least one port 103a/103b for draining fluid, in particular water, from the filtrate chamber $F_{1F}$ of the first hollow fiber membrane filter, a fluid line 112 for draining fluid, in particular water, from the filtrate chamber, a first valve connection V1 in engagement with the fluid line for draining fluid, in particular water, from the retentate chamber $F_{1R}$ of the first hollow fiber membrane filter F1, and a sampling point P1 downstream of the first valve connection.

FIG. 1 shows further details of the apparatus for treating fluids, in particular water for dialysis. FIG. 1 therefore shows a second hollow fiber membrane filter F2 having a retentate chamber $F_{2R}$ and a filtrate chamber $F_{2F}$ formed by the membrane wall of the plurality of hollow fiber membranes. FIG. 1 further shows a fluid port 120 for supplying fluid, in particular water, to the retentate chamber $F_{2R}$ of the second hollow fiber membrane filter F2, the fluid port 121 and fluid line 130 for draining fluid, in particular water, from the retentate chamber $F_{2R}$ of the second hollow fiber membrane filter F2, at least one fluid port 103a/103b and fluid line 131 for draining fluid, in particular water, from the filtrate chamber $F_{2F}$ of the second hollow fiber membrane filter F2, an extraction point E, as well as seventh V7, eighth V8, ninth V9, and tenth V10 valve connections for further supporting the treatment of fluids, in particular water, in the apparatus according to the invention.

According to the inventive method, fluid, in particular water, is treated by fluid, in particular water, being introduced into the retentate chamber $F_{1R}$ of the first hollow fiber membrane filter via fluid line 110 and fluid port 101. The position of the first valve V1 is thereby set to a flow-blocking valve position. Water can be introduced by way of pumping means which are not depicted in the present FIG. 1. The fluid is carried through the membrane wall $F_{1M}$ into the filtrate chamber $F_{1F}$ of the first hollow fiber membrane filter F1 and led via fluid ports 103a/b, 120 and fluid line 112 into the retentate chamber $F_{2R}$ of the second hollow fiber membrane filter F2 in order to provide a treated fluid, in particular water for producing a dialysis fluid, as applicable in a further "tangential flow" filtration.

The retentate chamber $F_{1R}$ of the first hollow fiber membrane filter is checked for contamination by the setting of valve connection V1 being brought into a conducting position. The concentrated contaminants in the retentate chamber $F_{1R}$ of the first hollow fiber membrane filter F1 can in this way be drained off via fluid line 111. Samples can be taken at sampling point P1 and supplied to the contamination analysis so that a conclusion can be made as to the contamination of the retentate chamber $F_{1R}$ of the first hollow fiber membrane filter F1. A (not shown) evaluation unit can be provided in the apparatus, or dialysis machine respectively, which monitors the filtered volume. Since the retentate flush volume can also be monitored, it is thus possible for a conversion factor to be given with which the initial microbe concentration of the unfiltered water can be determined, for example in CFU(ml). The eighth V8, ninth V9 and tenth V10 valve connections can thereby be brought into conducting or blocking position in order to support the sampling. For a sampling at sampling point P1, the eighth valve connection V8 and the tenth valve connection are set to a blocking position and the ninth valve connection V9 to a conducting position.

Figure 2:
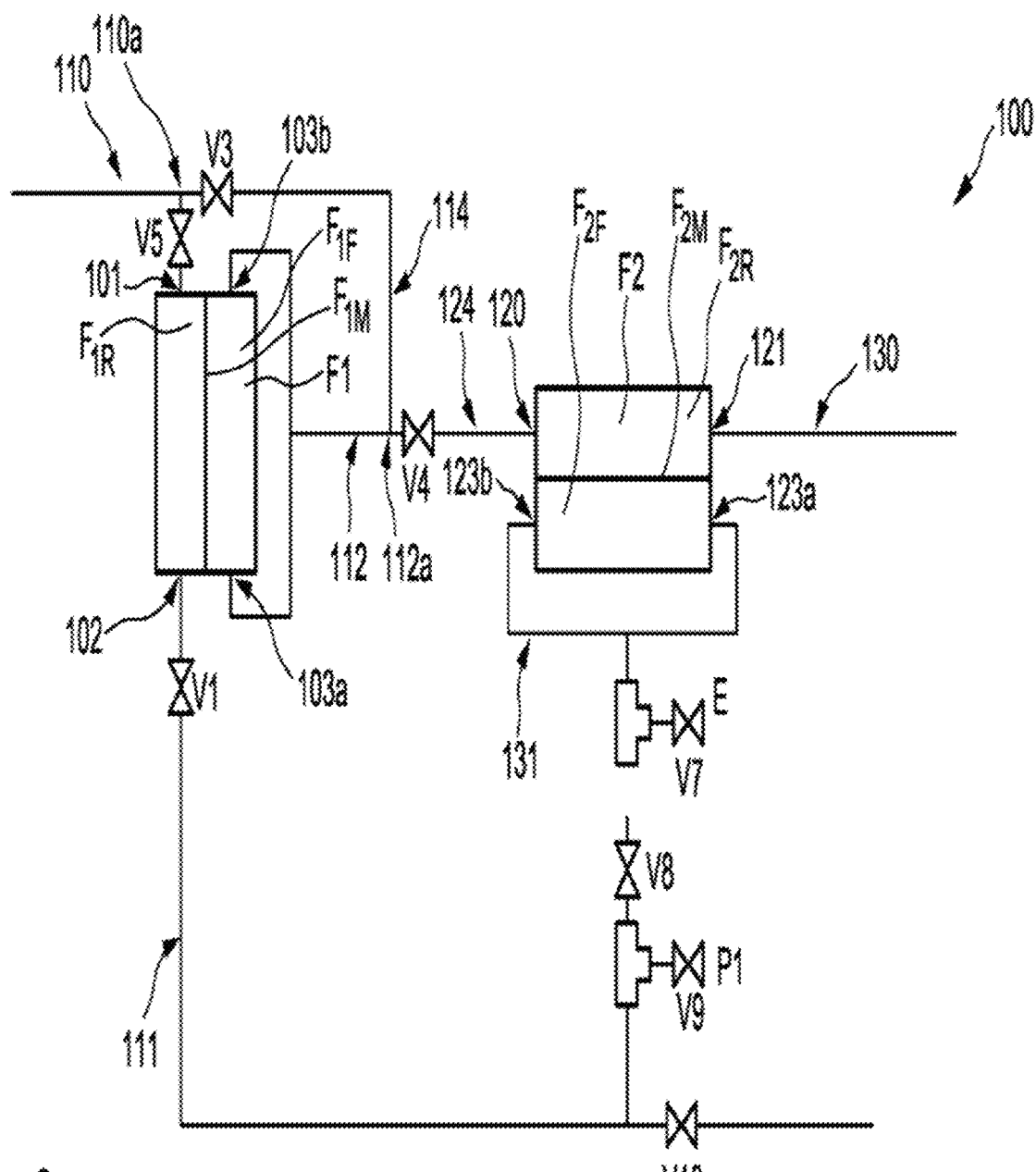
FIG. 2 is a schematic depiction of another apparatus for treating fluids, in particular, water for dialysis, in accordance with another embodiment of the present invention.

FIG. 2 shows a schematic depiction of a further embodiment of the inventive apparatus for the treatment of fluids, in particular water. FIG. 2 shows, additionally to that as in FIG. 1, a first fluid branching point 111a in the fluid line 111 for draining fluid from the retentate chamber $F_{1R}$ of the first hollow fiber membrane filter F1, a first branching fluid line 113 from fluid branching point 111a, a valve connection V2 in engagement with said fluid line and a sampling point P2 in fluid communication with the fluid line 113, as well as an eleventh valve connection V11. To treat the fluid, valve connections V1 and V2 are set to a blocking position. Fluid, in particular water, is introduced into the retentate chamber $F_{1R}$ of the first hollow fiber membrane filter F1 and carried through the membrane wall $F_{1M}$ into the filtrate chamber $F_{1F}$ of the first hollow fiber membrane filter F1. The fluid accumulating in the filtrate chamber $F_{1F}$ is carried into the retentate chamber $F_{1R}$ of the second hollow fiber membrane filter by fluid ports 103a/b, 120 and fluid line 112 in order to provide a treated fluid, in particular water for producing a dialysis fluid, as applicable in a further "tangential flow" filtration.

The retentate chamber $F_{1R}$ of the first hollow fiber membrane filter can be checked for contamination by the setting of valve connection V2 being put into a conducting position. The contaminants concentrated in the retentate chamber $F_{1R}$ of the first hollow fiber membrane filter F1 can in this way be drained via fluid line 113. Samples can be taken at sampling point P2 and supplied to the analysis. The eleventh valve V11 is set to conducting position for sampling.

Figure 3:
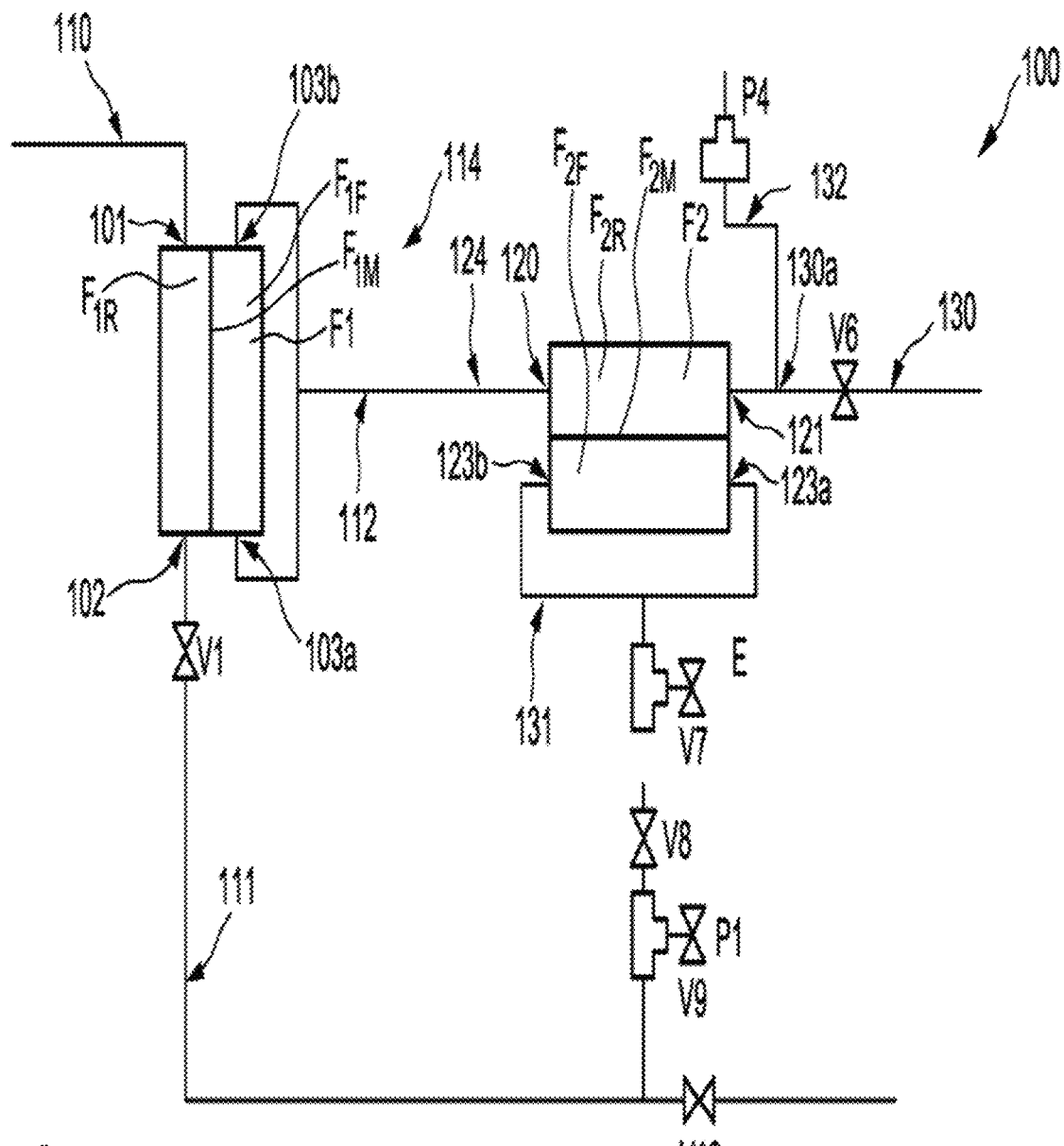
FIG. 3 is a schematic depiction of yet another apparatus for treating fluids, in particular, water for dialysis, in accordance with yet another embodiment of the present invention.

FIG. 3 shows a further schematic depiction of a further embodiment of the inventive apparatus 100 for treating fluids, in particular water. FIG. 3 shows, additionally to that as in FIG. 1, a fifth valve connection in engagement with the fluid line 110 for supplying fluid, in particular water, to the retentate chamber $F_{1R}$ of the first hollow fiber membrane filter, a second fluid branching point 110a and a third fluid branching point 112a in the fluid line 112 for draining fluid, in particular water, from the filtrate chamber $F_{1F}$ of the first hollow fiber membrane filter F1, a fluid line 114 in fluid communication with the second fluid branching point 110a and the third fluid branching point 112a, as well as a third valve connection V3 in engagement with fluid line 114 fluidly connected to the second fluid branching point 110a and the third fluid branching point 112a.

The fluid is treated by means of fluid, in particular water, being introduced into the retentate chamber $F_{1R}$ of the first hollow fiber membrane filter F1, whereby the fifth valve connection V5 is set to a conducting position and the third V3 and the first V1 valve connections are set to a blocking position. Fluid, in particular water, is introduced into the retentate chamber $F_{1R}$ of the first hollow fiber membrane filter via fluid line 110 and fluid port 101. Water can be introduced by way of pumping means which are not depicted in the present FIG. 3. The fluid is carried through the membrane wall $F_{1M}$ into the filtrate chamber $F_{1F}$ of the first hollow fiber membrane filter F1 and led via fluid ports 103a/b, 120 and fluid line 112 into the retentate chamber $F_{2R}$ of the second hollow fiber membrane filter F2. The fourth valve connection is in a conducting valve position. As necessary, a treated fluid, in particular water for producing a dialysis fluid, is provided a further "tangential flow" filtration on the second hollow fiber membrane filter F2.

In accordance with the FIG. 3 depiction, a "preflushing process" can be used to check the apparatus according to the invention for contamination of the retentate chamber $F_{1R}$. The fifth and the first valve connection V5 and V1 are accordingly set to a conducting valve position and the third and fourth valve connection V3 and V4 are set to a blocking valve position. In this arrangement of the valve connections and valve positions, concentrated contaminants can be drained from the retentate chamber $F_{1R}$ of the first hollow fiber membrane filter. Samples can be taken at sampling point P1 and analyzed for contamination.

In accordance with the FIG. 3 depiction, a "backflushing process" can also be used to check for contamination of the retentate chamber $F_{1R}$ of the first hollow fiber membrane filter. For this, the fifth valve connection V5 and the fourth valve connection V4 are set to a blocking valve position and the third valve connection V3 and the first valve connection V1 to a conducting valve position. Fluid, in particular water, is then introduced into the filtrate chamber $F_{1F}$ of the first hollow fiber membrane filter F1 via fluid lines 110, 114, 112 and fluid ports 103a/b and carried through the membrane wall $F_{1M}$ into the retentate chamber $F_{1R}$ of the first hollow fiber membrane filter F1. The fluid, in particular water, accumulating in the retentate chamber $F_{1R}$ is drained along with the contaminants concentrated in the retentate chamber $F_{1R}$ via fluid line 111. Samples can be taken at sampling point P1 and supplied to the analysis so that conclusions can be made as to the contamination of the retentate chamber $F_{1R}$ of the first hollow fiber membrane filter F1. A combined preflushing and backflushing process is preferential so as to be able to check the concentrated contaminants in the retentate chamber $F_{1R}$ of the first hollow fiber membrane filter F1. In particular, the backflushing process enables contaminants which adhere to the membrane wall $F_{1M}$ in the retentate chamber $F_{1R}$ to be flushed out and provided to the analysis.

Figure 4:
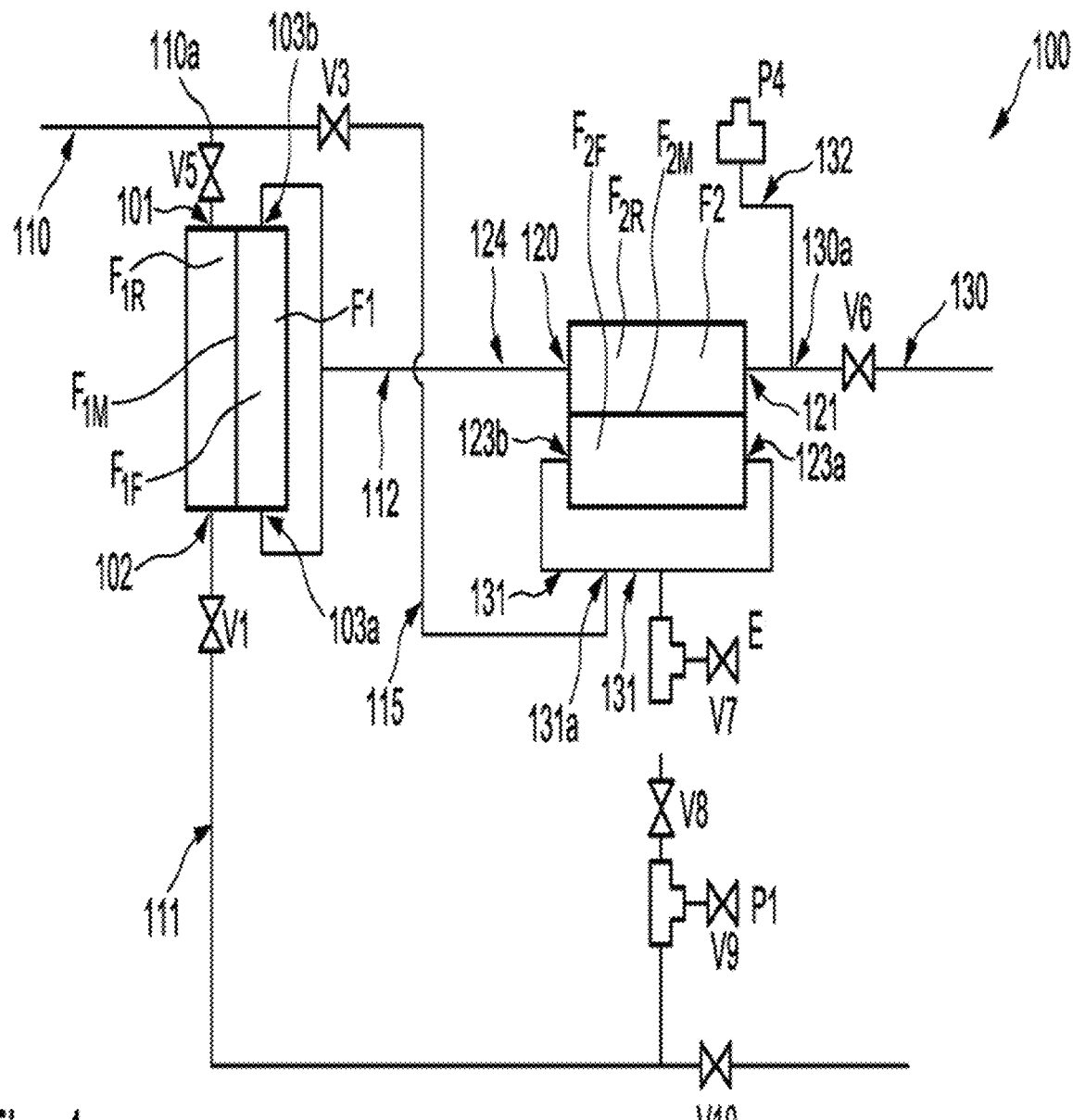
FIG. 4 is a schematic depiction of yet another apparatus for treating fluids, in particular, water for dialysis, in accordance with yet another embodiment of the present invention.

FIG. 4 shows a further schematic depiction of a further embodiment of the inventive apparatus 100 for treating fluids, in particular water. FIG. 4 shows, additionally to that as in FIG. 1, a fourth fluid branching point 130a, a sixth valve connection V6 in engagement with the fluid line 130 for draining fluid, in particular water, from the retentate chamber F.sub.2R of the second hollow fiber membrane filter F2 and a second branching fluid line 132 which brings the fourth fluid branching point 130a into fluid communication with a fourth sampling point P4. Sampling point P4 serves in the sampling of fluid, in particular water, drained from the retentate chamber F.sub.2R of the second hollow fiber membrane filter F2 in order to be able to determine contaminants by analysis.

The fluid is treated by way of fluid, in particular water, being introduced into the retentate chamber $F_{1R}$ of the first hollow fiber membrane filter via fluid line 110 and fluid port 101. The position of the first valve connection is set to a blocking valve position. The fluid, in particular water, can be introduced into the retentate chamber $F_{1R}$ by pumping means which are not depicted in the present FIG. 4. The fluid is carried through the membrane wall $F_{1M}$ into the filtrate chamber $F_{1F}$ of the first hollow fiber membrane filter F1 and led via fluid ports 103a/b, 120 and fluid line 112 into the retentate chamber $F_{2R}$ of the second hollow fiber membrane filter F2. In a further step, fluid, in particular water, is processed in the second hollow fiber membrane filter F2 by the "tangential flow method". In the process, fluid, in particular water, is introduced into the retentate chamber $F_{2R}$ of the second hollow fiber membrane filter F2 via fluid line 112 and fluid port 120 as described above, whereby the sixth valve connection V6 is brought into a conducting valve position. A portion of the fluid, in particular water, introduced into the retentate chamber $F_{2R}$ of the second hollow fiber membrane filter passes into the filtrate chamber $F_{2F}$ of the second hollow fiber membrane filter under the "tangential flow" method and can be drained off via fluid ports 123a/b and fluid line 131 and sampled at extraction point E, e.g. to produce a substituate fluid or to retrieve samples for the contamination analysis, provided the seventh valve connection V7 is brought into a conducting valve position. A further portion of the fluid, in particular water, which was introduced in the retentate chamber $F_{2R}$ of the second hollow fiber membrane filter is drained off via fluid port 121 and fluid line 130 and can be further processed, e.g. to produce a dialysis fluid.

The fluid, in particular water, drained from the retentate chamber $F_{2R}$ of the second hollow fiber membrane filter can be checked for contamination by the sixth valve connection V6 being brought into a blocking valve position, samples being taken at sampling point P4 are the samples analyzed for contamination. The apparatus thus enables analyzing the fluid, in particular water, obtained by "dead-end" filtration on the first hollow fiber membrane filter F1.

In yet a further embodiment of the inventive apparatus 100 for treating fluids, in particular water, and in contrast to FIG. 3, there is no third fluid branching 112 in the fluid line for draining fluid from the filtrate chamber $F_{1F}$ of the first hollow fiber membrane filter F1. Furthermore, the apparatus has no fluid line 114 bringing the second fluid branching point 110a into fluid communication with the third fluid branching point 112a of the apparatus according to FIG. 3. As opposed to the implementation in FIG. 3, the apparatus is characterized by a fifth fluid branching point 131a being arranged in the fluid line 131 for draining fluid, in particular water, from the filtrate chamber $F_{2F}$ of the second hollow fiber membrane filter F2. In accordance with the arrangement pursuant to this further embodiment, the apparatus is further characterized by a fluid line bringing the second fluid branching point 110a into fluid communication with the fifth fluid branching point 131a.

In accordance with the previous descriptions, the apparatus according to the further embodiment serves in the water treatment of fluid, particularly water, wherein treatment on the first hollow fiber membrane filter F1 ensues pursuant to "dead-end" filtration and treatment on the second hollow fiber membrane filter pursuant to the "tangential flow" method. By setting the fifth and the first valve connection to a conducting valve position and setting valve connection V3 to a blocking valve position, samples can be taken via sampling point P1 and analyzed for contamination so that conclusions can be made as to the contamination of the retentate chamber $F_{1R}$ of the first hollow fiber membrane filter F1.

By setting the first valve connection V1 and the sixth valve connection V6 to a blocking valve position and setting the fifth valve connection V5 to a conducting valve position, samples can be taken via sampling point P4 and analyzed for contamination so that conclusions can be made as to the contamination of the filtrate chamber $F_{1F}$ of the first hollow fiber membrane filter, fluid line 112, and the retentate chamber $F_{2R}$ of the second hollow fiber membrane filter.

By setting the fifth valve connection V5 and the first valve connection V1 to a blocking valve position and setting the third valve connection V3 to a conducting valve position, fluid is introduced via fluid line 110 for supplying fluid to the retentate chamber $F_{1R}$ of the first hollow fiber membrane filter and fluid line 115 which brings the second fluid branching point 110a into fluid communication with the fifth fluid branching point 131a via fluid line 131 into the filtrate chamber $F_{2F}$ and is carried through the membrane wall $F_{2M}$ of the second hollow fiber membrane filter F2 into the retentate chamber $F_{2R}$ of the second hollow fiber membrane filter. With this valve arrangement and valve position setting, the filtration of fluid, in particular water, at the second hollow fiber membrane filter F2 ensues from the filtrate chamber into the retentate chamber of the second hollow fiber membrane filter pursuant the principle of back-flushing. Backflushing the second hollow fiber membrane filter F2 can flush out the contami-nants which adhere to the membrane wall F2M of the second hollow fiber membrane filter. Samples can be taken via sampling point P4 and analyzed for contamination. The analysis allows conclusions as to the contamination of the second hollow fiber membrane filter.

The invention claimed is:

1. A method for monitoring a treatment of water for dialysis, comprising the steps of
providing an apparatus for treating the water for dialysis, the apparatus comprising
a first hollow fiber membrane filter, wherein the first hollow fiber membrane filter further comprises
a plurality of hollow fiber membranes which form a retentate chamber and a filtrate chamber, wherein the retentate chamber and the filtrate chamber are separated from each other by semipermeable membrane walls of the hollow fiber membranes,
a fluid port for supplying the water to the retentate chamber,
a fluid port for draining the water from the retentate chamber,
at least one fluid port for draining filtered water from the filtrate chamber,
wherein the apparatus further comprises
a fluid line in fluid communication with the fluid port for supplying the water, to the retentate chamber of the first hollow fiber membrane filter,
a fluid line in fluid communication with the fluid port for draining the water, from the retentate chamber of the first hollow fiber membrane filter,
a fluid line in fluid communication with the fluid port for draining the filtered water, from the filtrate chamber of the first hollow fiber membrane filter,
a first valve connection in engagement with the fluid line for draining the water, from the retentate chamber, wherein the first valve connection has at least two valve positions by means of which a flow of water through the fluid line for draining the water from the retentate chamber, can be blocked or conducted,
a first fluid branching point in the fluid line for draining the water, from the retentate chamber of the first hollow fiber membrane filter in fluid communication with a first branching fluid line, a second valve connection in engagement with the first branching fluid line, wherein the second valve connection has at least two valve positions by means of which the flow of water through the first branching fluid line, can be blocked or conducted, and
a sampling point arranged downstream of the first valve connection and being in fluid communication with the fluid line for draining the water, from the retentate chamber, and/or a second sampling point arranged downstream of the second valve connection and being in fluid communication with the first branching fluid line, wherein the method further comprises the steps of:

setting the first valve connection and the second valve connection into respective blocking positions, introducing the water, into the retentate chamber of the first hollow fiber membrane filter, filtering the water, across the semipermeable membrane walls of the hollow fiber membranes from the retentate chamber to the filtrate chamber of the first hollow fiber membrane filter to form the filtered water in the filtrate chamber, and collecting the filtered water in the filtrate chamber whereby contaminants in the water are retained by the hollow fiber membranes during filtration, draining the filtered water, from the filtrate chamber, and either (i) setting the first valve connection to a conducting position after a predetermined volume of filtered water has passed into the filtrate chamber by filtration, wherein the second valve connection remains in the blocking position, introducing further water, into the retentate chamber of the first hollow fiber membrane filter, and taking samples at the sampling point downstream of the first valve connection and analyzing the samples for contamination, or (ii) setting the first valve connection to the blocking position and setting the second valve connection to a conducting position after the predetermined volume of filtered water has passed into the filtrate chamber of the first hollow fiber membrane filter by filtration, introducing the further water, into the retentate chamber of the first hollow fiber membrane filter, and taking second samples at the second sampling point downstream of the first fluid branching point and analyzing the second samples for contamination.

2. The method according to claim 1, wherein the predetermined volume of water, passed by filtration into the filtrate chamber of the first hollow fiber membrane filter, amounts to at least 20 liters or more.

3. A method for monitoring a treatment of water for dialysis, comprising the steps providing an apparatus for treating the water for dialysis, the apparatus comprising a first hollow fiber membrane filter, wherein the first hollow fiber membrane filter further comprises a plurality of hollow fiber membranes which form a retentate chamber and a filtrate chamber, wherein the retentate chamber and the filtrate chamber are separated from each other by semipermeable membrane walls of the hollow fiber membranes, a fluid port for supplying the water to the retentate chamber, a fluid port for draining the water from the retentate chamber, and at least one fluid port for draining filtered water from the filtrate chamber, wherein the apparatus further comprises a fluid line in fluid communication with the fluid port for supplying the water to the retentate chamber of the first hollow fiber membrane filter, a fluid line in fluid communication with the fluid port for draining the water from the retentate chamber of the first hollow fiber membrane filter, a fluid line in fluid communication with the fluid port for draining the filtered water from the filtrate chamber of the first hollow fiber membrane filter, a first valve connection in engagement with the fluid line for draining the water from the retentate chamber, wherein the first valve connection has at least two valve positions, by means of which a flow of fluid through the fluid line for draining the water from the retentate chamber, can be blocked or conducted, a first fluid branching point in the fluid line for draining the water, from the retentate chamber of the first hollow fiber membrane filter, and being in fluid communication with a first branching fluid line, a second valve connection in engagement with the first branching fluid line, wherein the second valve connection has at least two valve positions by means of which the flow of water through the first branching fluid line, can be blocked or conducted, a sampling point arranged downstream of the first valve connection and being in fluid communication with the fluid line for draining the water, from the retentate chamber, and/or a second sampling point arranged downstream of the second valve connection and being in fluid communication with the first branching fluid line, a second fluid branching point arranged in the fluid line for supplying water, to the retentate chamber upstream of the first hollow fiber membrane filter, and a third fluid branching point arranged in the fluid line for draining water from the filtrate chamber of the first hollow fiber membrane filter, wherein the second fluid branching point on the fluid line for supplying the water, into the retentate chamber of the first hollow fiber membrane filter, and the third fluid branching point on the fluid line for draining the filtered water from the filtrate chamber of the first hollow fiber membrane filter, are fluidly connected by a fluid line, a third valve connection is arranged in engagement with the fluid line between the second fluid branching point and the third fluid branching point, the third valve connection has at least two valve positions by means of which the flow of water through the fluid line between the second fluid branching point and the third fluid branching point, can be blocked or conducted, and a fourth valve connection is arranged downstream the third fluid branching point in engagement with the fluid line for draining the filtered water, from the filtrate chamber, the fourth valve connection has at least two valve positions by means of which a flow of the filtered water through the fluid line for draining the filtered water from the filtrate chamber, can be blocked or conducted and the method further comprises the steps of:

setting the first valve connection to a blocking valve position, setting the third valve connection to a blocking valve position, setting the fourth valve connection to a conducting valve position, introducing the water, into the retentate chamber of the first hollow fiber membrane filter, filtering the water, across the semipermeable membrane walls of the hollow fiber membranes of the first hollow fiber membrane filter, whereby contaminants in the water, are retained by the semipermeable membrane walls of the hollow fiber membranes during the filtration, passing the water, from the filtrate chamber of the first hollow fiber membrane filter to a retentate chamber of a second hollow fiber membrane filter, filtering the water, in the retentate chamber of the second hollow fiber membrane filter through semipermeable membrane walls of hollow fiber membranes of the second hollow fiber membrane filter, to form twice filtered water, whereby contaminants in the fluid are retained by the semipermeable membrane walls of the hollow fiber membranes of the second hollow fiber membrane filter during the filtration, draining the twice filtered water out of a filtrate chamber of the second hollow fiber membrane filter, drawing samples at an extraction point connected to the fluid line for draining twice filtered water from the filtrate chamber of the second hollow fiber membrane filter, and analyzing the samples as to contamination, subsequently setting the first valve connection to a conducting position, setting the third valve connection to a conducting position, setting the fourth valve connection to a blocking position, after a predetermined volume of water, has passed to the filtrate chamber by filtration, filtering the water, in the filtrate chamber of the first hollow fiber membrane filter through the semipermeable membrane walls of the hollow fiber membranes of the first hollow fiber membrane filter into the retentate chamber of the first hollow fiber membrane filter, whereby contaminants are flushed from the retentate chamber of the first hollow fiber membrane filter during the filtration, draining fluid out of the retentate chamber of the first hollow fiber membrane filter, and taking samples of water at the sampling point downstream of the first valve connection and analyzing the samples of water as to contamination.

4. A method for monitoring a treatment of water for dialysis, comprising the steps providing an apparatus for treating the water for dialysis, the apparatus comprising a first hollow fiber membrane filter, wherein the first hollow fiber membrane filter further comprises a plurality of hollow fiber membranes which form a retentate chamber and a filtrate chamber, wherein the retentate chamber and the filtrate chamber are separated from each other by semipermeable membrane walls of the hollow fiber membranes, a fluid port for supplying the water to the retentate chamber, a fluid port for draining the water from the retentate chamber, and at least one fluid port for draining filtered water from the filtrate chamber, wherein the apparatus further comprises a fluid line in fluid communication with the fluid port for supplying the water, to the retentate chamber of the first hollow fiber membrane filter, a fluid line in fluid communication with the fluid port for draining the water, from the retentate chamber of the first hollow fiber membrane filter, a fluid line in fluid communication with the fluid port for draining the filtered water, from the filtrate chamber of the first hollow fiber membrane filter, a first valve connection in engagement with the fluid line for draining the water, from the retentate chamber, wherein the first valve connection has at least two valve positions by means of which a flow of water through the fluid line for draining the water from the retentate chamber, can be blocked or conducted, a first fluid branching point in the fluid line for draining the water, from the retentate chamber of the first hollow fiber membrane filter in fluid communication with a first branching fluid line, a second valve connection in engagement with the first branching fluid line, wherein the second valve connection has at least two valve positions by means of which the flow of water through the first branching fluid line, can be blocked or conducted, a sampling point arranged downstream of the first valve connection and being in fluid communication with the fluid line for draining the water, from the retentate chamber, and/or a second sampling point arranged downstream of the second valve connection and being in fluid communication with the first branching fluid line, a second fluid branching point arranged in the fluid line for supplying the water, to the retentate chamber upstream of the first hollow fiber membrane filter, and a third fluid branching point arranged in the fluid line for draining the filtered water from the filtrate chamber of the first hollow fiber membrane filter, wherein the second fluid branching point on the fluid line for supplying the water into the retentate chamber of the first hollow fiber membrane filter, and the third fluid branching point on the fluid line for draining the filtered water from the filtrate chamber of the first hollow fiber membrane filter, are fluidly connected by a fluid line, a third valve connection is arranged in engagement with the fluid line between the second fluid branching point and the third fluid branching point, the third valve connection has at least two valve positions by means of which the flow of water through the fluid line between the second fluid branching point and the third fluid branching point, can be blocked or conducted, a fourth valve connection is arranged downstream the third fluid branching point in engagement with the fluid line for draining the filtered water from the filtrate chamber, wherein the fourth valve connection has at least two valve positions by means of which the flow of water through the fluid line for draining the filtered water from the filtrate chamber, can be blocked or conducted, and a fifth valve connection is arranged upstream of the first hollow fiber membrane filter between the second fluid branching point on the fluid line for supplying the water to the retentate chamber of the first hollow fiber membrane filter, and the first hollow fiber membrane filter in engagement with the fluid line for supplying the water to the retentate chamber of the first hollow fiber membrane filter, wherein the fifth valve connection has at least two valve positions by means of which the flow of water through the fluid line for supplying the water to the retentate chamber of the first hollow fiber membrane filter, can be blocked or conducted, and the method further comprises the steps of:

setting the first valve connection to a blocking position,
setting the fifth valve connection to a conducting position,
setting the third valve connection to a blocking position,
setting the fourth valve connection to a conducting position,
introducing the water, into the retentate chamber of the first hollow fiber membrane filter,
filtering the water, through the semipermeable membrane walls of the hollow fiber membranes of the first hollow fiber membrane filter, to form the filtered water in the filtrate chamber, whereby contaminants in the water are retained by the semipermeable membrane walls of the hollow fiber membranes during the filtration,
passing the filtered water, from the filtrate chamber of the first hollow fiber membrane filter, to a second retentate chamber of a second hollow fiber membrane filter, the second hollow fiber membrane filter comprising the second retentate chamber and a second filtrate chamber,
filtering the filtered water, in the retentate chamber of the second hollow fiber membrane filter, through membrane walls of hollow fiber membranes of the second hollow fiber membrane filter, whereby contaminants in the filtered water are retained by the membrane walls of the hollow fiber membranes of the second hollow fiber membrane filter during the filtration, to form twice filtered water in the second filtrate chamber,
draining the twice filtered water out of the second filtrate chamber of the second hollow fiber membrane filter,
drawing samples at the extraction point connected to a fluid line for draining the twice filtered water from the second filtrate chamber of the second hollow fiber membrane filter, and analyzing the samples as to contamination,
subsequently setting the first valve connection to a conducting position,
setting the fifth valve connection to a blocking position,
setting the third valve connection to a conducting position,
setting the fourth valve connection to a blocking position,
after a predetermined volume of water, has passed to the filtrate chamber of the first hollow fiber membrane filter by filtration, filtering the water, in the filtrate chamber of the first hollow fiber membrane filter through the semipermeable membrane walls of the hollow fiber membranes of the first hollow fiber membrane filter into the retentate chamber of the first hollow fiber membrane filter, whereby contaminants are flushed from the retentate chamber of the first hollow fiber membrane filter during the filtration,
draining fluid out of the retentate chamber of the first hollow fiber membrane filter, and
taking samples at the sampling point downstream of the first valve connection and analyzing the samples of the sampling point.

5. A method for monitoring a treatment of water for dialysis, comprising the steps providing an apparatus for treating the water for dialysis, the apparatus comprising a first hollow fiber membrane filter, wherein the first hollow fiber membrane filter further comprises
a plurality of hollow fiber membranes which form a retentate chamber and a filtrate chamber, wherein the retentate chamber and the filtrate chamber are separated from each other by semipermeable membrane walls of the hollow fiber membranes,
a fluid port for supplying the water to the retentate chamber,
a fluid port for draining the water from the retentate chamber,
at least one fluid port for draining filtered water from the filtrate chamber, wherein the apparatus further comprises
a fluid line in fluid communication with the fluid port for supplying the water, to the retentate chamber of the first hollow fiber membrane filter,
a fluid line in fluid communication with the fluid port for draining the water, from the retentate chamber of the first hollow fiber membrane filter,
a fluid line in fluid communication with the fluid port for draining the filtered water, from the filtrate chamber of the first hollow fiber membrane filter,
a first valve connection in engagement with the fluid line for draining the water, from the retentate chamber, wherein the first valve connection has at least two valve positions by means of which a flow of water through the fluid line for draining the water from the retentate chamber, can be blocked or conducted,
a first fluid branching point in the fluid line for draining the water, from the retentate chamber of the first hollow fiber membrane filter in fluid communication with a first branching fluid line, a second valve connection in engagement with the first branching fluid line, wherein the second valve connection has at least two valve positions by means of which a flow of water through the first branching fluid line, can be blocked or conducted,
a sampling point arranged downstream of the first valve connection and being in fluid communication with the fluid line for draining the water, from the retentate chamber, and/or a second sampling point arranged downstream of the second valve connection and being in fluid communication with the first branching fluid line,
a second hollow fiber membrane filter, wherein the second hollow fiber membrane filter comprises a plurality of hollow fiber membranes having semipermeable membrane walls, a retentate chamber, and a filtrate chamber, the retentate chamber and the filtrate chamber being separated from each other by semipermeable membrane walls of the hollow fiber membranes,
a fluid port for supplying the filtered water into the retentate chamber of the second hollow fiber membrane filter,
a fluid port for draining the filtered water from the retentate chamber of the second hollow fiber membrane filter,
at least one fluid port for draining twice filtered water from the filtrate chamber of the second hollow fiber membrane filter,
a fluid line in fluid communication with the fluid port for supplying filtered water into the retentate chamber of the second hollow fiber membrane filter, a fluid line in fluid communication with the fluid port for draining the filtered water from the retentate chamber of the second hollow fiber membrane filter, and a fluid line in fluid communication with the at least one fluid port for draining the twice filtered water from the filtrate chamber of the second hollow fiber membrane filter, wherein the fluid line in fluid communication with the fluid port for supplying the filtered water into the retentate chamber of the second hollow fiber membrane filter is fluidly connected to the fluid line for draining the filtered water from the filtrate chamber of the first hollow fiber membrane filter, wherein a fourth fluid branching point is arranged in the fluid line between the fluid port for draining the filtered water from the retentate chamber of the second hollow fiber membrane filter, a second branching fluid line branches from the fourth fluid branching point and is fluidly connected to the fourth fluid branching point, a sixth valve connection is in engagement with the fluid line for draining the filtered water from the retentate chamber of the second hollow fiber membrane filter and is arranged downstream of the fourth fluid branching point, the sixth valve connection has at least two valve positions by means of which flow of filtered water through the fluid line for draining the filtered water from the retentate chamber of the second hollow fiber membrane filter, can be blocked or conducted, and the second branching fluid line is in fluid communication with a third sampling point, wherein the method further comprises the steps of:

setting the first valve connection to a blocking position, setting the sixth valve connection to a conducting position, introducing the water, into the retentate chamber of the first hollow fiber membrane filter, filtering the water, through the semipermeable membrane walls of the hollow fiber membranes of the first hollow fiber membrane filter, from the retentate chamber of the first hollow fiber membrane filter to the filtrate chamber of the first hollow fiber membrane filter, collecting the filtered water in the filtrate chamber of the first hollow fiber membrane filter, whereby contaminants in the water, are retained by the hollow fiber membranes during the filtering of the water, passing the filtered water, from the filtrate chamber of the first hollow fiber membrane filter to the retentate chamber of the second hollow fiber membrane filter, setting the sixth valve connection to a blocking position after a predetermined volume of water has passed to the filtrate chamber of the first hollow fiber membrane filter, by filtration, introducing further water into the retentate chamber of the first hollow fiber membrane filter, filtering the further water in the filtrate chamber of the first hollow fiber membrane filter, to form further filtered water, passing the further filtered water from the filtrate chamber of the first hollow fiber membrane filter to the retentate chamber of the second hollow fiber membrane filter, and taking third samples at the third sampling point and analyzing the third samples as to contamination.

6. A method for monitoring a treatment of water for dialysis, comprising the steps providing an apparatus for treating the water for dialysis, the apparatus comprising a first hollow fiber membrane filter, wherein the first hollow fiber membrane filter further comprises a plurality of hollow fiber membranes which form a retentate chamber and a filtrate chamber, wherein the retentate chamber and the filtrate chamber are separated from each other by semipermeable membrane walls of the hollow fiber membranes, a fluid port for supplying the water to the retentate chamber, a fluid port for draining the water from the retentate chamber, at least one fluid port for draining filtered water from the filtrate chamber, wherein the apparatus further comprises a fluid line in fluid communication with the fluid port for supplying the water, to the retentate chamber of the first hollow fiber membrane filter, a fluid line in fluid communication with the fluid port for draining the water, from the retentate chamber of the first hollow fiber membrane filter, a fluid line in fluid communication with the fluid port for draining the filtered water, from the filtrate chamber of the first hollow fiber membrane filter, a first valve connection in engagement with the fluid line for draining the water, from the retentate chamber, wherein the first valve connection has at least two valve positions by means of which a flow of water through the fluid line for draining the water from the retentate chamber, can be blocked or conducted, a first fluid branching point in the fluid line for draining the water, from the retentate chamber of the first hollow fiber membrane filter in fluid communication with a first branching fluid line, a second valve connection in engagement with the first branching fluid line, wherein the second valve connection has at least two valve positions by means of which a flow of water through the first branching fluid line, can be blocked or conducted, a sampling point arranged downstream of the first valve connection and being in fluid communication with the fluid line for draining the water, from the retentate chamber, and/or a second sampling point arranged downstream of the second valve connection and being in fluid communication with the first branching fluid line, at least one second hollow fiber membrane filter, wherein the second hollow fiber membrane filter further comprises a plurality of hollow fiber membranes forming a retentate chamber and a filtrate chamber which are separated from each other by a semipermeable membrane wall of the hollow fiber membranes, a fluid port for supply of the filtered water, into the retentate chamber of the second hollow fiber membrane filter, a fluid port for draining of the filtered water, from the retentate chamber of the second hollow fiber membrane filter, at least one fluid port for draining twice filtered water from the filtrate chamber of the second hollow fiber membrane filter, and wherein the apparatus further comprises
at least one fluid line for supplying the water, into the retentate chamber of the second hollow fiber membrane filter,
at least one fluid line in fluid communication with the at least one fluid port for draining the twice filtered water from the filtrate chamber of the second hollow fiber membrane filter,
wherein a second fluid branching point is arranged in the fluid line for supplying the water, to the retentate chamber of the first hollow fiber membrane filter upstream of the first hollow fiber membrane filter, wherein the apparatus comprises a fifth fluid branching point on the fluid line for draining the twice filtered water from the filtrate chamber of the second hollow fiber membrane filter, wherein a fourth sampling point is arranged in fluid communication via a fourth fluid branching point in the fluid line for draining the filtered water from the retentate chamber of the second hollow fiber membrane filter, wherein
the arrangement of a fluid line in fluid communication with the second fluid branching point on the fluid line for supplying the water, into the retentate chamber of the first hollow fiber membrane filter and the fifth fluid branching point on the fluid line for draining the twice filtered water from the filtrate chamber of the second hollow fiber membrane filter, wherein a third valve connection is arranged in engagement with the fluid line between the second fluid branching point on the fluid line for supplying the water, into the retentate chamber of the first hollow fiber membrane filter, and the fifth fluid branching point on the fluid line for draining the twice filtered water from the filtrate chamber of the second hollow fiber membrane filter, wherein the third valve connection has at least two valve positions, by means of which a flow of water, through the fluid line between the second fluid branching point and the fifth fluid branching point can be blocked or conducted, wherein
the fluid port for supplying filtered water to the retentate chamber of the second hollow fiber membrane filter is in fluid communication with the at least one fluid port for draining the filtered water from the filtrate chamber of the first hollow fiber membrane filter via a fluid line, wherein
a fifth valve connection is arranged upstream the first hollow fiber membrane filter between the second fluid branching point in engagement with the fluid line for supplying the water, into the retentate chamber of the first hollow fiber membrane filter, wherein the fifth valve connection has at least two valve positions, by means of which a flow of water, in the fluid line for supplying the water, to the retentate chamber of the first hollow fiber membrane filter can be blocked or conducted,
wherein the method further comprises the steps of:
setting the first valve connection to a blocking position,
setting the fifth valve connection to a conducting position,
setting the third valve connection to a blocking position,
setting the sixth valve connection to a conducting position,
introducing the water into the retentate chamber of the first hollow fiber membrane filter,
filtering the water through the semipermeable membrane walls of the hollow fiber membranes of the first hollow fiber membrane filter from the retentate chamber of the first hollow fiber membrane filter to the filtrate chamber of the first hollow fiber membrane filter, to form the filtered water, and collecting the filtered water in the filtrate chamber of the first hollow fiber membrane filter, whereby contaminants in the water are retained by the hollow fiber membranes of the first hollow fiber membrane filter, during the filtering of the water,
passing the filtered water from the filtrate chamber of the first hollow fiber membrane filter to the retentate chamber of the second hollow fiber membrane filter,
filtering the filtered water through the semipermeable membrane wall of the hollow fiber membranes of the second hollow fiber membrane filter from the retentate chamber of the second hollow fiber membrane filter to the filtrate chamber of the second hollow fiber membrane filter, to form twice filtered water, and collecting the twice filtered water in the filtrate chamber of the second hollow fiber membrane filter, whereby contaminants in the filtered water are retained by the hollow fiber membranes of the second hollow fiber membrane filter, during the filtration to form the twice filtered water,
draining the twice filtered water out of the filtrate chamber of the second hollow fiber membrane filter, drawing a third sample at an extraction point connected to the fluid line for draining the water from the filtrate chamber of the second hollow fiber membrane filter, and analyzing the third sample as to contamination,
subsequently setting the fifth valve connection to a blocking position,
setting the third valve connection to a conducting position,
setting the sixth valve connection to a blocking position,
and, after a predetermined volume of filtered water has passed to the filtrate chamber of the second hollow fiber membrane filter, by filtration, introducing fresh water into the filtrate chamber of the second hollow fiber membrane filter, flushing the fresh water through the semipermeable membrane wall of the hollow fiber membranes of the second hollow fiber membrane filter from the filtrate chamber of the second hollow fiber membrane filter to the retentate chamber of the second hollow fiber membrane filter,
collecting the flushed fresh water in the retentate chamber of the second hollow fiber membrane filter, whereby contaminants that had been retained by the hollow fiber membranes of the second hollow fiber membrane filter are flushed out of the retentate chamber of the second hollow fiber membrane filter during the filtration, and
taking samples at the fourth sampling point and analyzing the samples as to contamination.

* * * * *